(12) United States Patent
Wu et al.

(10) Patent No.: US 9,568,426 B2
(45) Date of Patent: Feb. 14, 2017

(54) CABINET CAPABLE OF GUIDING LIGHT

(71) Applicant: SMOBIO TECHNOLOGY, INC., Hsinchu (TW)

(72) Inventors: Chen-Sheng Wu, Hsinchu (TW); Chun-Hsien Kuo, Hsinchu (TW); Kuan-Lin Lee, Hsinchu (TW)

(73) Assignee: SMOBIO TECHNOLOGY, INC., Hsinchu (TW)

( * ) Notice: Subject to any disclaimer, the term of this patent is extended or adjusted under 35 U.S.C. 154(b) by 163 days.

(21) Appl. No.: 14/271,226

(22) Filed: May 6, 2014

(65) Prior Publication Data

US 2015/0323725 A1  Nov. 12, 2015

(30) Foreign Application Priority Data

May 7, 2013 (TW) .............................. 102208493 U

(51) Int. Cl.
*F21V 15/00* (2015.01)
*G01N 21/64* (2006.01)
*F21V 8/00* (2006.01)

(52) U.S. Cl.
CPC ........ *G01N 21/6447* (2013.01); *G01N 21/645* (2013.01); *G02B 6/003* (2013.01); *G01N 2201/02* (2013.01); *G01N 2201/062* (2013.01); *G01N 2201/08* (2013.01)

(58) Field of Classification Search
CPC . F01N 21/645; G02B 6/003; G01N 2201/062; G01N 2201/02; G01N 21/6447; G01N 21/6428; G01N 2201/08; A47B 2200/0077; A47B 13/12; F21K 2/00; F21K 9/00; F21K 9/56; F21V 9/16; F21V 5/007; F21V 9/08; H01J 65/08; H05B 33/00; A47F 3/001; A47F 3/005; A47F 3/007; A47F 3/0434; A47F 3/0456; A47F 11/10

USPC ........................ 362/362, 125, 224, 333, 237, 311.1,362/133–134, 136–138, 140, 144; 250/453.11

See application file for complete search history.

(56) References Cited

U.S. PATENT DOCUMENTS

| | | | |
|---|---|---|---|
| 8,419,229 B2* | 4/2013 | Dong | F21V 5/04 362/296.01 |
| 2002/0191396 A1* | 12/2002 | Reiff | F21L 4/04 362/246 |
| 2010/0075408 A1* | 3/2010 | Waiche | G01N 21/6447 435/288.7 |
| 2012/0009088 A1* | 1/2012 | Yan | G01N 21/6452 422/82.08 |

* cited by examiner

*Primary Examiner* — Laura Tso
*Assistant Examiner* — Naomi M Wolford
(74) *Attorney, Agent, or Firm* — Tracy M. Heims; Apex Juris, pllc

(57) ABSTRACT

A cabinet capable of guiding light, which is used for detecting a biological sample strained with a fluorescent dye, includes a main body, at least one light source, and at least one light guiding structure. The main body has a sample table to place the biological sample. The at least one light source is provided on the main body and near the sample table, wherein the at least one light source provides light required to excite the fluorescent dye incorporated in the biological sample. The at least one light guiding structure is provided between the sample table and the at least one light source to refract the light provided by the at least one light source onto the sample table and the biological sample. Whereby, the biological sample is exposed to more light, and therefore the intensity of the light released from the biological sample is enhanced.

7 Claims, 7 Drawing Sheets

CABINET CAPABLE OF GUIDING LIGHT

BACKGROUND OF THE INVENTION

1. Technical Field

The present invention relates generally to bio-detection device, and more particularly to a cabinet which is capable of guiding light.

2. Description of Related Art

In the current field of biotechnology, fluorescence detection is a relative simple and most widely used method for detecting specific molecules in biological samples. In this method, particular fluorescent dyes such as Ethidium Bromide, SYPRO RUBY, and SYBR Green I are incorporated into biological samples. These fluorescent dyes can be excited by light of certain wavelengths to release visible light due to the effect of fluorescence resonance energy transfer (FRET). Therefore, researchers are able to perform certain naked eye observations in this way.

Ethidium Bromide is commonly used in early fluorescence detection, and this kind of fluorescent dyes has to be excited by ultraviolet rays in a dark room. Such experimental environment is harmful to researchers in the long term. Recent fluorescence detection typically takes SYPRO RUBY and SYBR Green I as fluorescent dyes, which can be excited by blue light in a normal laboratory. Researchers usually use blue light emitting diodes (LEDs) to provide the required blue light, and biological samples are placed on a dark background to make higher contrast for clearer observation.

However, the light released by fluorescent dyes is quite weak relative to the ambient light in a laboratory. One of the methods of increasing the intensity of the released light is to deploy more LEDs. In fact, such method only increases the area exposed under light, and is not really that helpful at enhancing the light intensity accepted by biological samples. Besides, a cabinet with more LEDs is clearly larger and heavier, and has higher cost.

BRIEF SUMMARY OF THE INVENTION

In view of the above, the primary objective of the present invention is to provide a cabinet, which is capable of guiding light provided by light sources onto a biological sample to increase the intensity of excitation light and then emission light released by fluorescent dyes incorporated in the biological sample.

The cabinet provided in the present invention is for detecting a biological sample which has incorporated with a fluorescent dye. The cabinet includes a main body, at least one light source, and at least one light guiding structure. The main body has a sample table to place the biological sample. The at least one light source is provided on the main body near the sample table, wherein the light source provides light to excite the fluorescent dye incorporated in the biological sample. The at least one light guiding structure is provided between the sample table and the at least one light source to refract the light provided by the light source onto the sample table.

Whereby, the intensity of light released from the biological sample is enhanced by refracting the light provided by the at least one light source onto the sample table, and especially onto the biological sample.

BRIEF DESCRIPTION OF THE SEVERAL VIEWS OF THE DRAWINGS

The present invention will be best understood by referring to the following detailed descriptions of some illustrative embodiments in conjunction with the accompanying drawings, in which.

DETAILED DESCRIPTION OF THE INVENTION

Figure 1:
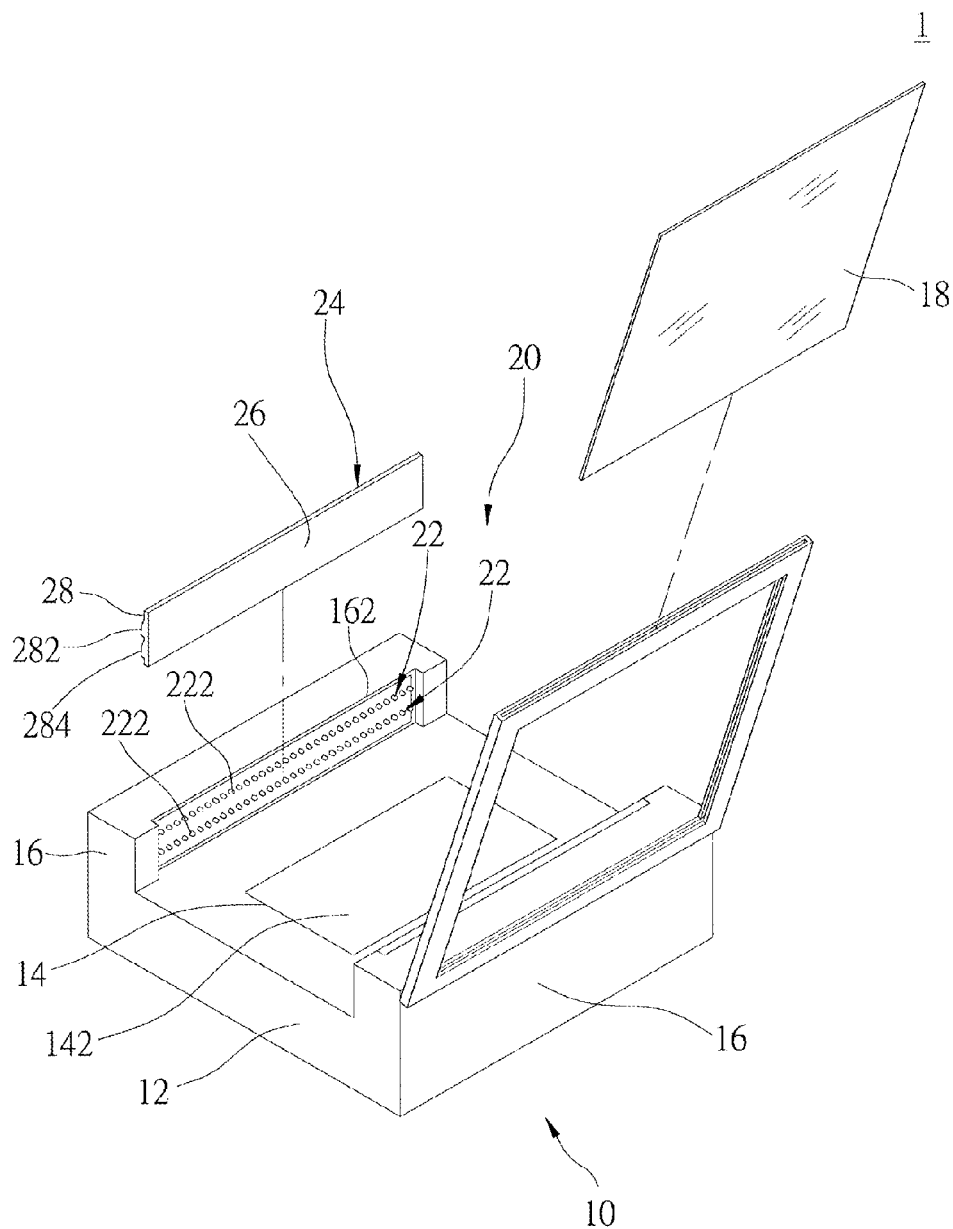
FIG. 1 is an exploded view of the cabinet of a first preferred embodiment of the present invention.
Figure 2:
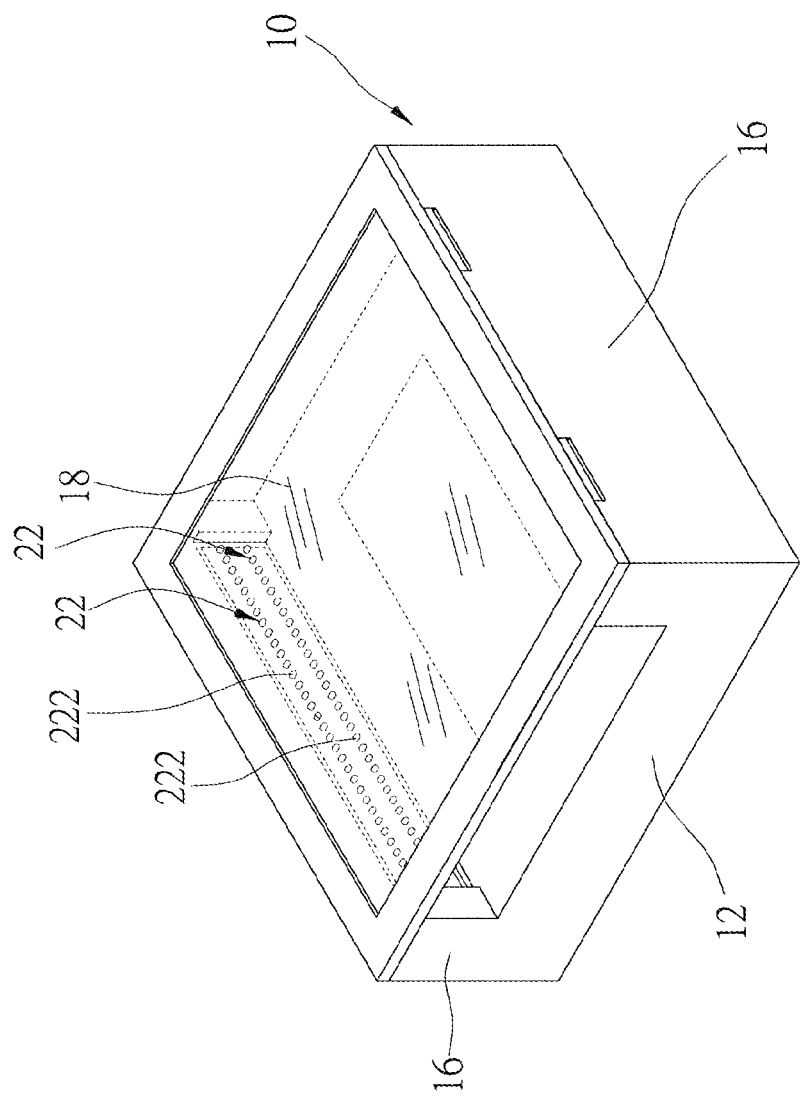
FIG. 2 is a perspective view of the cabinet of the first preferred embodiment of the present invention.
Figure 3:
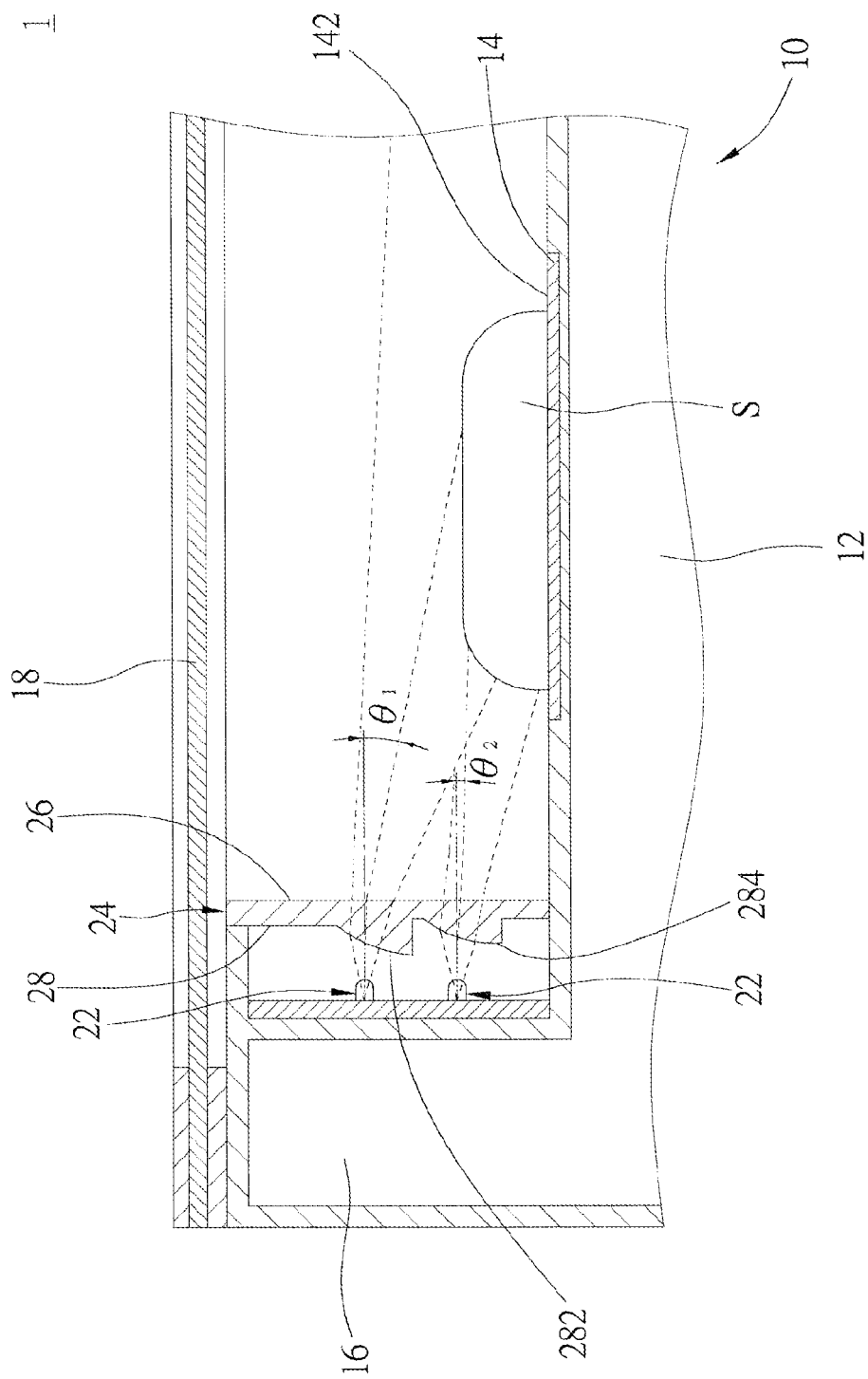
FIG. 3 is a partial sectional view of the cabinet of the first preferred embodiment of the present invention, showing the situation while the cabinet is being used.

As shown in FIG. 1 to FIG. 3, a cabinet 1 of the first preferred embodiment of the present invention is capable of guiding light, and is designed for detecting a biological sample S which has be strained with a fluorescent dye. The cabinet 1 includes a main body 10 and two light modules 20.

The main body 10 has a base 12 and two walls 16, which are respectively vertically connected to two opposite ends of the base 12. A top of the base 12 is provided with a plate 14, and a sample table 142 is formed on a top surface of the plate 14 to place the biological sample S. An inner side of each of the two walls 16 is respectively provided with an opening 162 thereon, and a rear optical filter 18 is provided at a top side of the two walls 16.

The two light modules 20 are respectively provided in each of the two walls 16, wherein each of the light modules 20 includes two light sources 22 and a light guiding plate 24. The light sources 22 are arranged in horizontal parallel, and each is composed of a plurality of light-emitting elements 222 which are arranged in parallel to the top surface 142 of the plate 14. The light-emitting elements 222 provide light to excite the fluorescent dye in the biological sample S. In the first preferred embodiment, the light-emitting elements 222 are blue LEDs. In addition, there is a power source (now shown) provided in the main body 10 to supply electricity to the blue LEDs.

Each of the light guiding plates 24 is a long rectangular transparent plate, which is respectively received in the opening 162 of one of the two walls 16. Each of the light guiding plates 24 has two opposite surfaces, which are an outer surface 26 and an inner surface 28, wherein the outer surface 26 faces the plate 14, and the inner surface 28 faces the light sources 22. In the first preferred embodiment, the outer surfaces 26 are both flat, and each of the inner surfaces 28 respectively has two lens portions 282, 284 arranged in horizontal parallel, and, more specifically, extended in a long} axial direction of the corresponding light guiding plate 24. Each of the lens portions 282, 284 respectively corresponds to one of the light sources 22, and has a convex surface extending from a top to a bottom thereof. The convex surface has a flat bottom which is substantially vertical to the inner surface 28. Each of the lens portions 282, 284 respectively forms a light guiding structure with a corresponding portion on the outer surface 26.

As shown in FIG. 3, the light provided by each of the light sources 22 enters the convex surface of the corresponding lens portion 282 or 284 (i.e., an incident surface of the light guiding structure) to be refracted for the first time; after that, the light is refracted again when it goes through the outer surface 26 of the light guiding plate 24 (i.e., an exit surface of the light guiding structure). Whereby, each of the light guiding structures bends the light provided by the corresponding light source 22 onto the biological sample S on the sample table 142 of the plate 14, and the fluorescent dye in the biological sample S is excited in this way. The released light from the fluorescent dye goes through the rear optical filter 18 for researchers to observe the biological sample S. Furthermore, the convex surface of each of the lens portions 282 or 284 can further converge the light, and therefore the light can be utilized more effectively.

As shown in FIG. 3, in the first preferred embodiment, a refraction angle $\theta_1$ of the light refracted by the upper light guiding structure is larger than a refraction angle $\theta_2$ of that refracted by the lower light guiding structure. Since the light provided by the upper light source 22 is reflected more downwardly, the biological sample S is exposed to more light. As to the lower light source 22, it is not necessary to dramatically bend the light provided by it. Because the lower light source 22 is already close to the biological sample S, it is much easier for its light to cover the biological sample S. This is why the refraction angle $\theta_2$ can be smaller.

With the aforementioned design, the intensity of the light released from the biological sample S is enhanced, which is helpful for performing observation. In practice, the inner surface 28 or the outer surface 26 of the light guiding plate 24 can be further coated with an optical filtering membrane, and the light guiding plate 24 can also be further provided with an optical filter, such as filtering dye, to filter out light of wavelengths which are outside a range of characteristic wavelengths of the fluorescent dye. In this way, unwanted light colors can be filtered out, and therefore the fluorescence generated by the fluorescent dye can be even easier to be observed.

Figure 4:
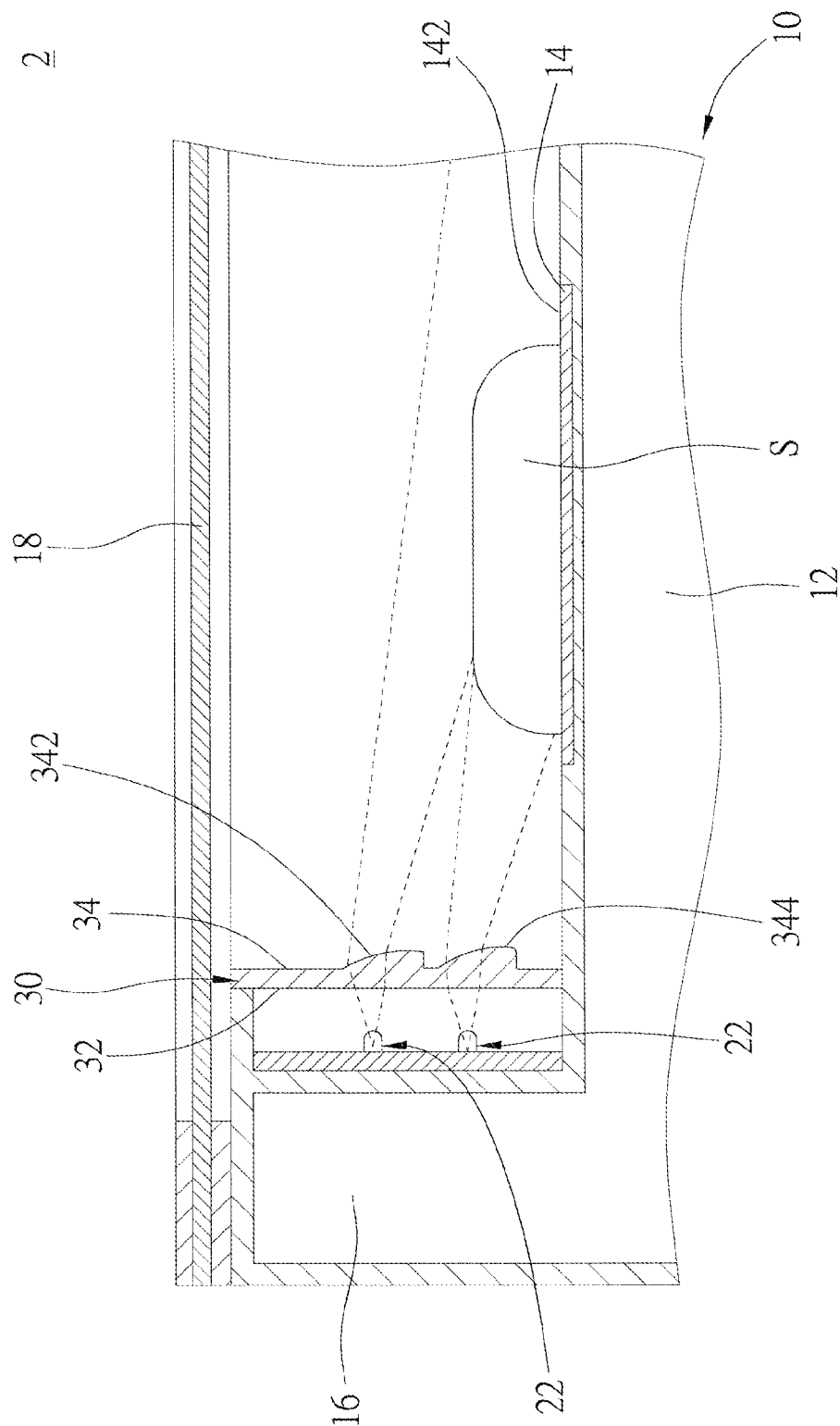
FIG. 4 is a partial sectional view of the cabinet of a second preferred embodiment of the present invention, showing the situation while the cabinet is being used.

As shown in FIG. 4, a cabinet 2 of the second preferred embodiment of the present invention has basically the same structure with that of the first preferred embodiment, excepting that an inner surface 32 of each of light guiding plates 30 in the second preferred embodiment is flat, and an outer surface 34 of each of light guiding plates 30 has a plurality of lens portions 342, 344 formed thereon, wherein the lens portions 342, 344 are arranged in horizontal parallel as well. Each of the lens portions 342, 344 and a corresponding portion on each of the inner surfaces 32 respectively forms a light guiding structure. While each of the corresponding portions on the inner surface 32 is an incident surface, a surface of each of the lens portions 342, 344 is an exit surface. Whereby, the light guiding plate 30 can also converge the light and bend it downwardly onto the biological sample S.

Figure 5:
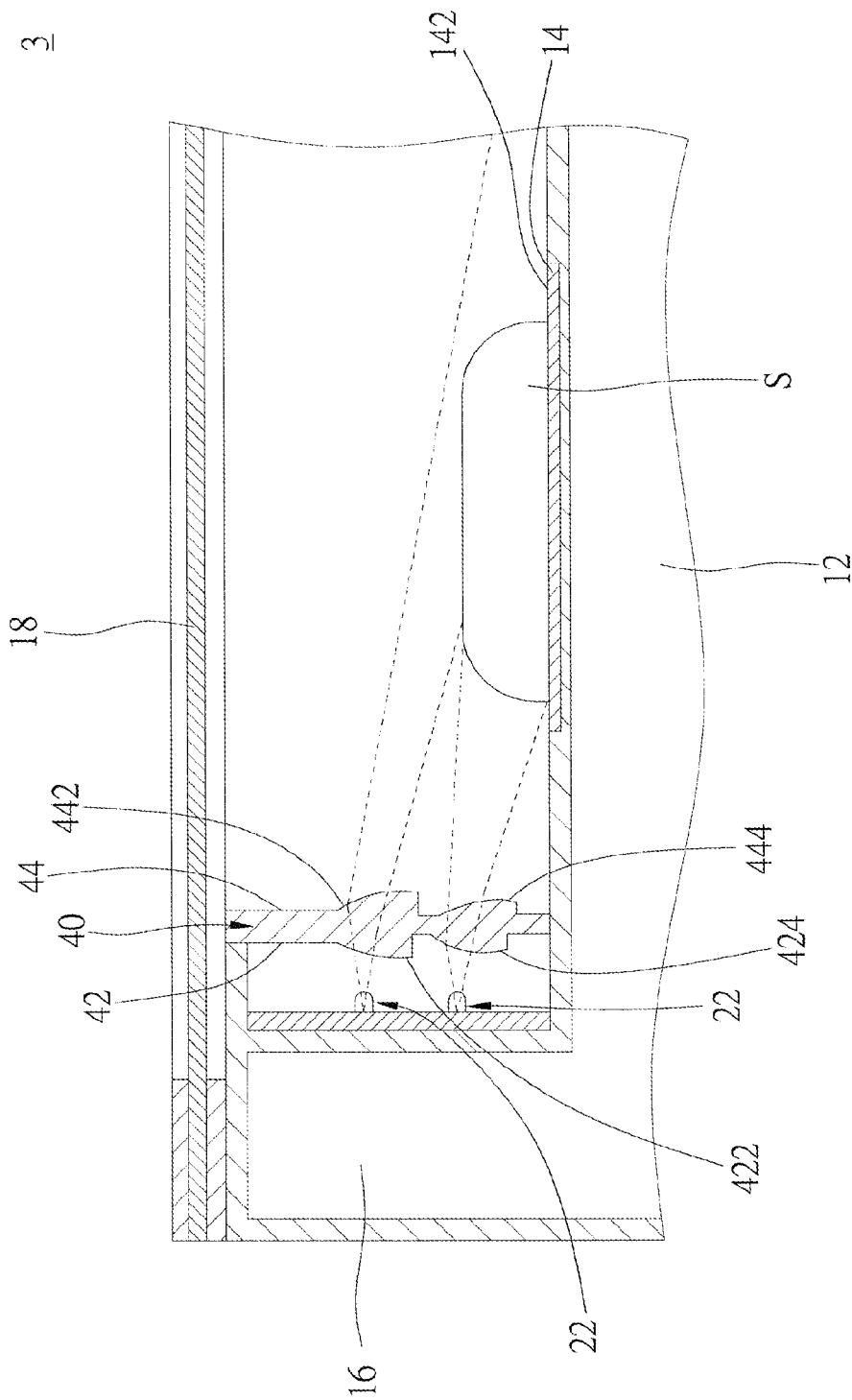
FIG. 5 is a partial sectional view of the cabinet of a third preferred embodiment of the present invention, showing the situation while the cabinet is being used.

As shown in FIG. 5, a cabinet 3 of the third preferred embodiment of the present invention also has basically the same structure with that of the first preferred embodiment, excepting that an inner surface 42 and an outer surface 44 of each of light guiding plates 40 in the third preferred embodiment both have a plurality of lens portions 422, 424, 442, 444 formed thereon, wherein the lens portions 422, 424 and the lens portions 442, 444 are respectively arranged in horizontal parallel. Each of the lens portions 422, 424 on the inner surface 42 and the corresponding lens portion 442 or 444 on the outer surface 44 forms a light guiding structure. While a surface of each of the lens portions 422, 424 on the inner surface 42 is an incident surface, a surface of each of the lens portions 442, 444 on the outer surface 44 is an exit surface. Similarly, the light guiding plate 40 can also converge the light and bend it downwardly.

In the aforementioned first to third preferred embodiments, the cabinets 1, 2, and 3 could only have the upper light guiding structure to bend the light provided by the upper light source 22 downwardly.

Figure 6:
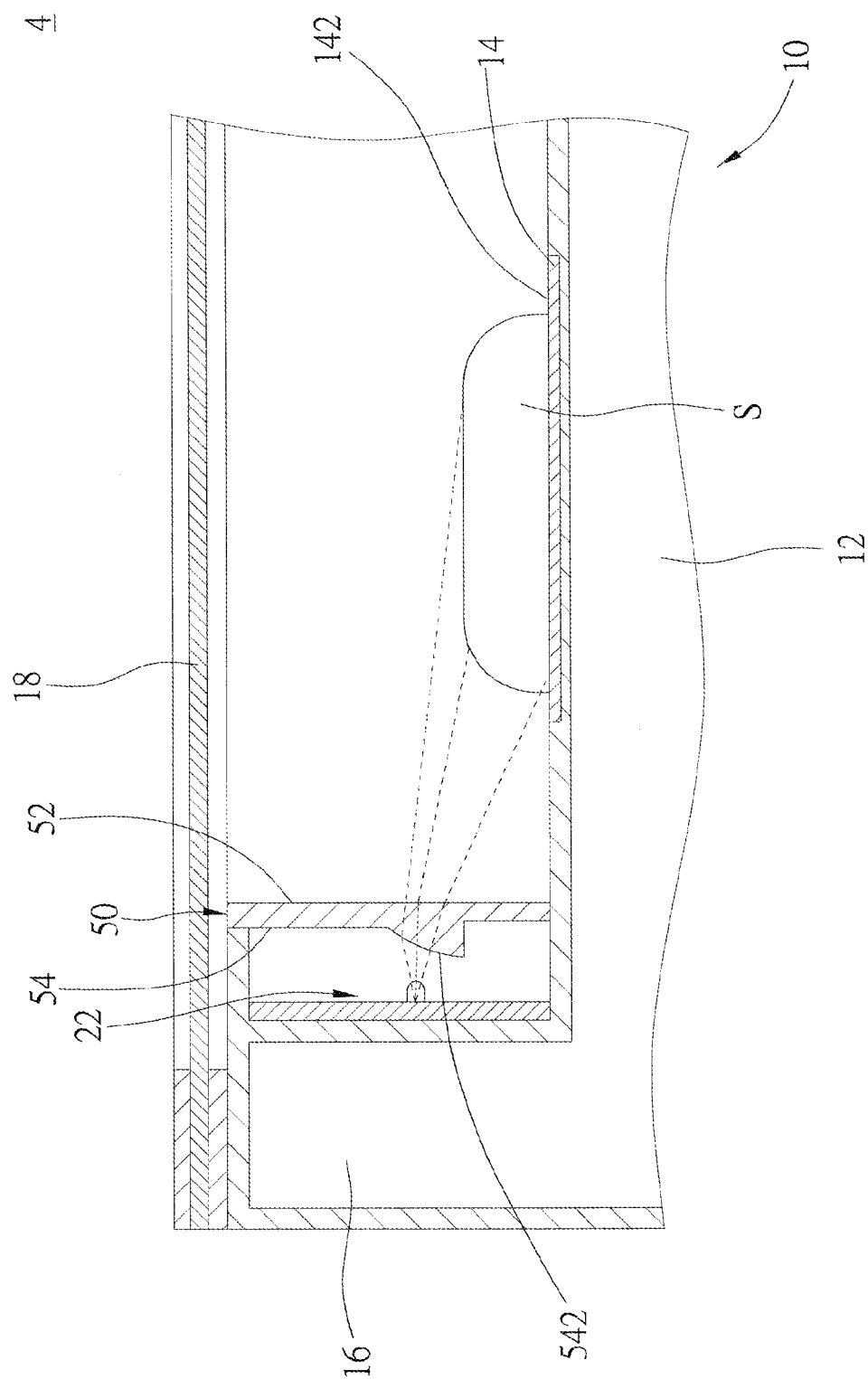
FIG. 6 is a partial sectional view of the cabinet of a fourth preferred embodiment of the present invention, showing the situation while the cabinet is being used.

As shown in FIG. 6, a cabinet 4 of the fourth preferred embodiment of the present invention also has basically the same structure with that of the first preferred embodiment, excepting that there is only one light source 22 applied in the fourth preferred embodiment, an outer surface 52 of each of light guiding plates 50 is flat, and only a single lens portion 542 formed on each of inner surfaces 54. Each of the lens portions 542 and a corresponding portion on each of the outer surfaces 52 forms a light guiding structure. The light guiding plate 50 can also converge the light and bend it downwardly. In practice, each of the lens portions 542 could be alternately formed on each of the outer surfaces 52, or on each of the outer surfaces 52 and each of the inner surfaces 54 at the same time.

Figure 7:
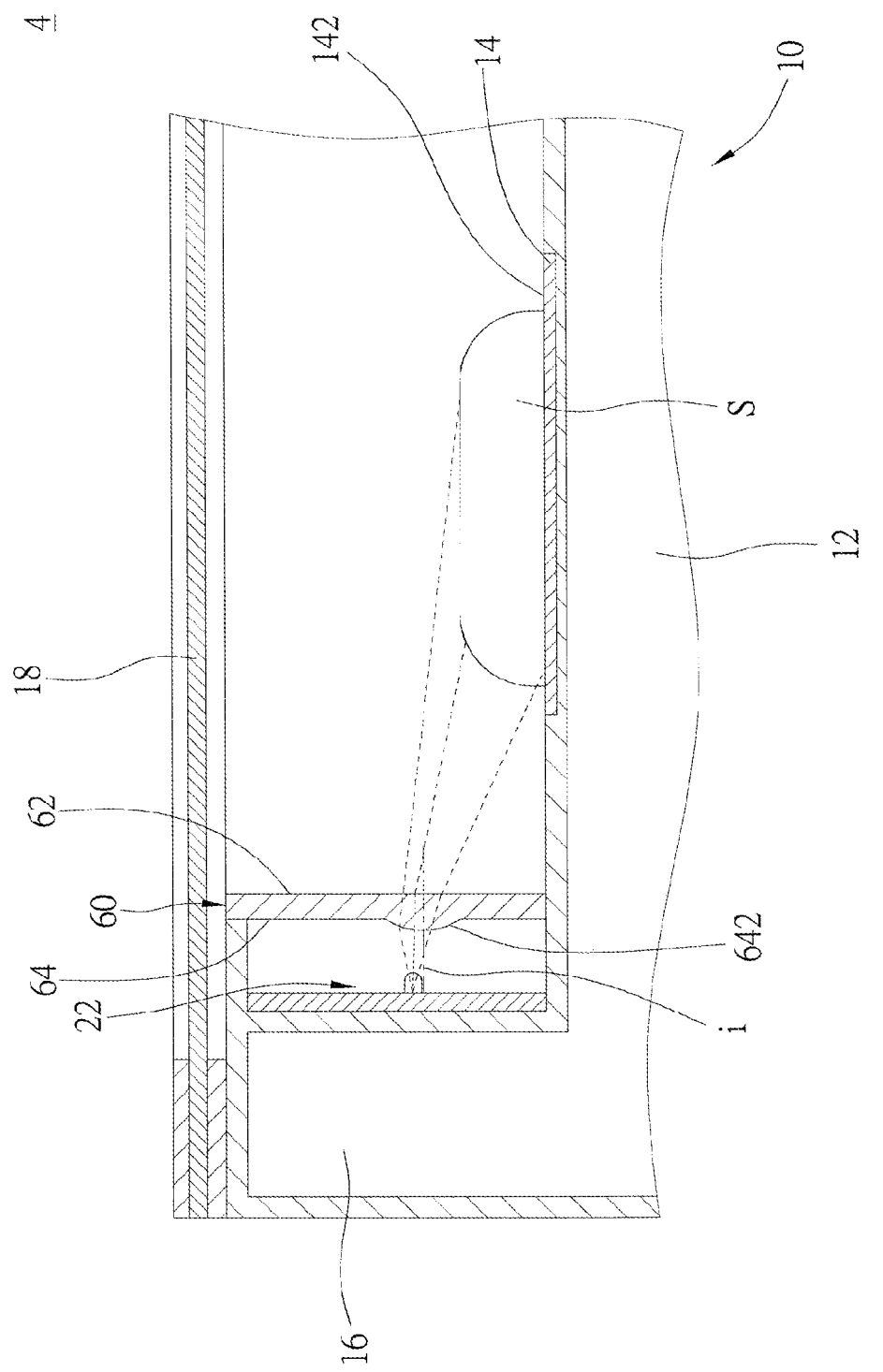
FIG. 7 is a partial sectional view of the cabinet of a fifth preferred embodiment of the present invention.

Besides, the light guiding plates 50 of the cabinet 4 can be replaced by light guiding plates 60 shown in FIG. 7. Each of the light guiding plates 60 also has an outer surface 62 and an inner surface 64, wherein the outer surface 62 is flat, and a surface of a lens portion 642 formed on the inner surface 64 is curved to form a light guiding structure of a convex lens. Specifically, where a central axial line of the light provided by the light source goes through the surface of the lens portion 642 is higher than a horizontal center line i of the lens portion 642. Whereby, the light is converged and bent downwardly after passing through each of the light guiding plates 60. Of course, the light guiding structure of the convex lens could be applied to all the aforementioned preferred embodiments as the light guiding plate thereof. The key point is, where the central axial line of the light provided by each light source goes through the surface of the corresponding lens portion has to be higher than the horizontal center line thereof.

In summary, the cabinets 1, 2, 3, and 4 provided in the present invention can effectively bend the light downwardly with the light guiding structures formed by the lens portions on the light guiding plates, and therefore the biological sample S can be exposed to more light, which enhances the intensity of the light released from the biological sample S. In addition, the numbers of the light sources and the light guiding structures are not limited as one or two. In other embodiments, the numbers can be three or more.

It must be pointed out that the embodiments described above are only some preferred embodiments of the present invention. All equivalent structures which employ the concepts disclosed in this specification and the appended claims should fall within the scope of the present invention.

What is claimed is:

1. A cabinet for detecting a biological sample strained with a fluorescent dye, comprising:
  a main body having a sample table to place the biological sample;

at least one light source provided on the main body near the sample table, wherein the light source provides light to excite the fluorescent dye in the biological sample;

at least one light guiding structure provided between the sample table and the at least one light source to refract the light provided by the light source onto the sample table; and a light guiding plate, wherein the light guiding plate has an inner surface facing the light sources and an outer surface which is opposite to the inner surface and faces the sample table; the outer surface is flat, and the inner surface has at least one lens portion formed thereon; each of the at least one lens portion and a corresponding portion on the outer surface respectively form one of the at least one light guiding structure;

wherein the at least one light source is positioned higher than a top surface of the biological sample, and the light provided by the at least one light source is directed downward after passing through the at least one light guiding structure;

wherein a surface of each of the at least one lens portion is curved, and is defined to have a horizontal center line, which is horizontally passing through a center of the surface; the light provided by each of the light sources is defined to have a central axial line, wherein when the light provided by each of the light sources passes through the corresponding portion, the central axial line thereof is higher than the horizontal center line of the surface of the corresponding lens portion.

2. The cabinet of claim 1, wherein the light guiding structure further converges the light provided by the light source onto the sample table.

3. The cabinet of claim 1, wherein the number of the at least one light source is more than one, and the light sources are arranged in horizontal parallel, including an upper light source and a lower light source; the light guiding structure refracts the light provided by the upper light source onto the sample table.

4. The cabinet of claim 3, wherein the number of the light guiding structure is more than one, and the light guiding structures are arranged in horizontal parallel axes along an upper line and a lower line, wherein each of the light guiding structures corresponds to one of the light sources to refract the light provided by the corresponding light source onto the sample table.

5. The cabinet of claim 4, wherein a refraction angle of the light refracted by the light guiding structures arranged in the upper line is larger than that refracted by those arranged in the lower line.

6. The cabinet of claim 1, wherein each of the at least one lens portion has a curved surface extending from a top to a bottom thereof.

7. The cabinet of claim 1, further comprising an optical filter provided on the light guiding plate to filter out light of wavelengths which are outside a range of characteristic wavelengths of the fluorescent dye.

* * * * *